United States Patent
Chen et al.

(10) Patent No.: US 10,295,481 B2
(45) Date of Patent: May 21, 2019

(54) DETECTION SYSTEM AND METHOD

(71) Applicants: Tsinghua University, Beijing (CN); NUCTECH COMPANY LIMITED, Beijing (CN)

(72) Inventors: Zhiqiang Chen, Beijing (CN); Li Zhang, Beijing (CN); Tianyi Yang Dai, Beijing (CN); Ji Zhao, Beijing (CN); Xin Jin, Beijing (CN); Ming Chang, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 243 days.

(21) Appl. No.: 15/262,894

(22) Filed: Sep. 12, 2016

(65) Prior Publication Data

US 2017/0176352 A1 Jun. 22, 2017

(30) Foreign Application Priority Data

Dec. 18, 2015 (CN) .......................... 2015 1 0958950

(51) Int. Cl.
*G01N 23/20* (2018.01)
*G01N 23/00* (2006.01)
(Continued)

(52) U.S. Cl.
CPC ......... *G01N 23/046* (2013.01); *G01N 23/083* (2013.01); *G01N 23/207* (2013.01);
(Continued)

(58) Field of Classification Search
CPC ........... G01N 23/201; G01N 2223/045; G01N 2223/056; G01N 2223/316;
(Continued)

(56) References Cited

U.S. PATENT DOCUMENTS 7,486,760 B2 * 2/2009 Harding ................. G01N 23/20
378/7
7,755,072 B2 7/2010 Porat
(Continued)

FOREIGN PATENT DOCUMENTS

CN 200941097 Y 8/2007
CN 101141918 A 3/2008
(Continued)

OTHER PUBLICATIONS

Extended European Search Report dated Apr. 18, 2017, in EP application No. 16185335.3 (7 pages).
(Continued)

*Primary Examiner* — Irakli Kiknadze
(74) *Attorney, Agent, or Firm* — Knobbe, Martens, Olson & Bear LLP

(57) ABSTRACT

The present disclosure relates to detection systems and methods. One illustrative detection system may include a distributed radiation source having a plurality of radiation source focus points, which irradiate an object under detection, wherein the plurality of radiation source focus points are divided into a certain number of groups, and a primary collimator that limits rays of each of the radiation source focus points such that the rays emit into an XRD detection device. An XRD detection device may include a plurality of XRD detectors that are divided into the same number of groups as the radiation source focus points, wherein XRD detectors in a same group are arranged to be separated by XRD detectors in other groups, and rays of each of the radiation source focus points are received by XRD detectors having the same group number as the group number of the radiation source focus point.

20 Claims, 7 Drawing Sheets

(51) Int. Cl.
*G01N 23/046* (2018.01)
*G01N 23/083* (2018.01)
*G01N 23/207* (2018.01)
*G21K 1/02* (2006.01)
*G01V 5/00* (2006.01)

(52) U.S. Cl.
CPC ..... *G01N 23/20083* (2013.01); *G01V 5/0025* (2013.01); *G21K 1/02* (2013.01); *G01N 2223/045* (2013.01); *G01N 2223/056* (2013.01); *G01N 2223/316* (2013.01); *G01N 2223/643* (2013.01); *G01V 5/005* (2013.01)

(58) Field of Classification Search
CPC ........... G01N 2223/643; G01N 23/046; G01N 23/083; G01N 23/20083; G01N 23/207; G01N 2223/419; G01N 2223/629; G01N 2223/66; G01N 23/09; G01N 2223/206; G01N 2223/401; G01N 2223/405; G01N 2223/41; G01N 2223/423; G01N 2223/63; G01N 23/20; G01N 23/20008; G01N 23/2076; G01N 2223/605; G01N 2223/0566; G01N 23/223; G01N 21/9501; G01V 5/0025; G01V 5/005; G01V 5/00; G01V 5/0041; H04L 63/0407; H04L 65/4023; H04L 65/4061; H04W 12/02; H04W 4/10; H04W 76/45; G02B 26/0875; G02B 26/106; G02B 5/18; G21K 1/02
USPC .................................. 378/4, 6, 7, 19, 70, 71
See application file for complete search history.

(56) References Cited

U.S. PATENT DOCUMENTS

| | | | |
|---|---|---|---|
| 7,787,591 B2 | 8/2010 | Harding et al. | |
| 7,869,566 B2* | 1/2011 | Edic | G01V 5/005 378/57 |
| 7,924,978 B2 | 4/2011 | Harding | |
| 8,477,904 B2* | 7/2013 | Blaj | G01N 23/046 378/71 |
| 2006/0210016 A1 | 9/2006 | Francke | |
| 2008/0013684 A1 | 1/2008 | Harding | |
| 2010/0061512 A1* | 3/2010 | Edic | G01N 23/20 378/71 |
| 2010/0135462 A1 | 6/2010 | Harding | |
| 2011/0188632 A1 | 8/2011 | Harding et al. | |
| 2012/0051510 A1 | 3/2012 | Ohta et al. | |
| 2015/0085973 A1 | 3/2015 | Li et al. | |
| 2017/0075026 A1 | 3/2017 | Chen et al. | |

FOREIGN PATENT DOCUMENTS

| | | |
|---|---|---|
| CN | 101512385 A | 8/2009 |
| CN | 101592622 A | 12/2009 |
| CN | 102004111 A | 4/2011 |
| CN | 102397076 A | 4/2012 |
| CN | 104458771 A | 3/2015 |
| CN | 104897703 A | 9/2015 |
| JP | 2010223836 A | 10/2010 |
| WO | WO 2005/120354 A1 | 12/2005 |

OTHER PUBLICATIONS

Harding et al., "X-ray diffraction computed tomography" Medical Physics Jul. 14, 1987, No. 4, New York NY, pp. 515-525 (11 pages).
International Search Report and Written Opinion dated Nov. 16, 2016 in PCT Appln. No. PCT/CN2016/095815 (13 pgs), and English-language translation of ISR (4 pgs); 17 pages total.
Office Action issued is corresponding Chinese Patent Application No. 201510958950.X, dated Jan. 29, 2019.

* cited by examiner

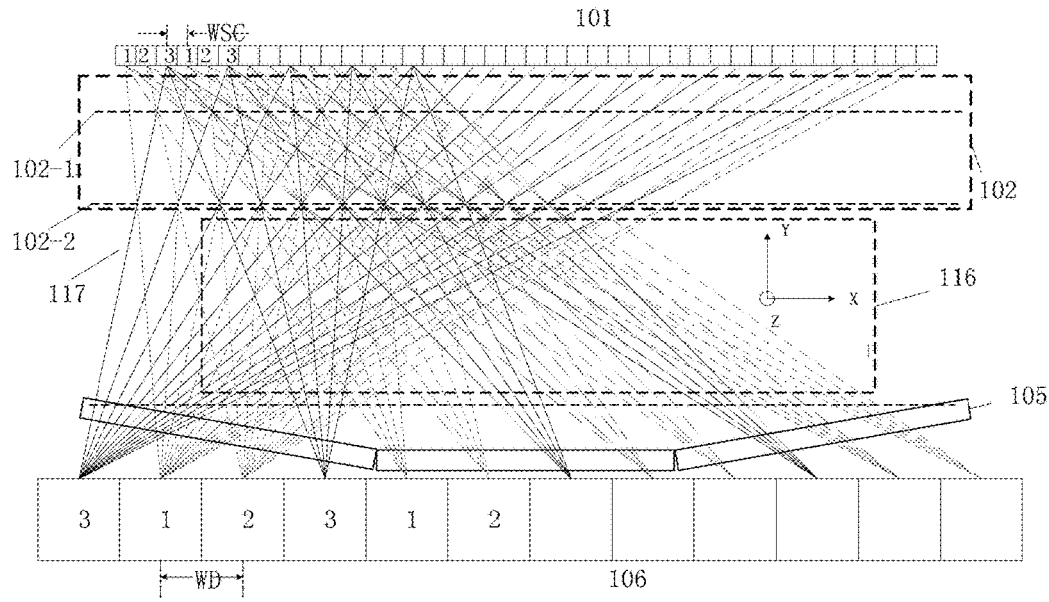

FIG. 13

200 irradiating, by a distributed radiation source, an object under detection, wherein the distributed radiation source has a plurality of radiation source focus points and the radiation source focus points are divided into a certain number of groups — S201 dividing a plurality of XRD detectors of an XRD detection device into the same number of groups as the radiation source focus points, wherein XRD detectors in a same group are arranged to be separated by XRD detectors in other groups — S202 controlling, by a primary collimator when each of the radiation source focus points is emitting rays, the rays emitted by the radiation source focus point such that the rays are merely received by XRD detectors having the same group number as the radiation source focus point in the plurality of XRD detectors — S203

FIG. 14

DETECTION SYSTEM AND METHOD

CROSS REFERENCE TO RELATED APPLICATION(S)

This application is based upon and claims benefit/priority to Chinese Patent Application No. 201510958950.X, filed on Dec. 18, 2015, published as CN106896121A, which is hereby incorporated by reference in its entirety.

BACKGROUND

Technical Field

The present disclosure relates to the technical field of imaging, and more particularly, to a detection system and method.

Description of the Related Art

In current radiation imaging techniques, X-ray transmission imaging and X-ray diffraction imaging has become two common non-destructive testing methods. These two X-ray imaging technologies may be used separately, and may also be used in combination in order to improve detection accuracy.

With respect to the combined use of these two techniques, a two-stage detection system has been disclosed in U.S. Pat. No. 7,924,978 B2 and U.S. Pat. No. 7,869,566 B2. In such a two-stage detection system, a stage of X-ray Computed Tomography (CT) detection may be performed firstly, and then another stage of X-ray Diffraction (XRD) detection is performed. However, such a two-stage detection system actually is combined of two independent systems, each of which utilizes an independent radiation source. Thus, the system is bulky and the usage of the radiation source is low. Moreover, such a two-stage detection system needs to precisely control a position of a suspicious region between the two independent systems. Accordingly, the detection efficiency thereof will be relatively low.

Further, U.S. Pat. No. 7,787,591 B2 discloses an XRD detection system in which transmission imaging can be performed in multiple angles at the same time. Although this system only uses one set of radiation source, this system actually is a quasi-3D chromatographic detection system and the radiation source has a limited range of distribution angle, which makes it difficult to achieve the same imaging quality as the CT imaging technique.

Further, US2011/0188632A1 discloses an XRD detection system. In this system, a primary collimator separate rays for the XRD detection onto multiple planes; a scattering collimator which has multiple leaves and slits in parallel (similar to Sola Slits) receives scattered rays from scattering centers at different depths; and the scattering collimator and detectors are arranged in a staggered manner to reduce impact of crosstalk.

OVERVIEW OF SOME ASPECTS

According to one aspect of the present disclosure, there is provided a detection system, comprising: a distributed radiation source having a plurality of radiation source focus points, which emit rays to irradiate an object under detection, wherein the plurality of radiation source focus points are divided into a certain number of groups; a primary collimator configured to limit rays of each of the radiation source focus points such that the rays emit into an XRD detection device; and the XRD detection device including a plurality of XRD detectors, wherein the plurality of XRD detectors are divided into the same number of groups as the radiation source focus points, and XRD detectors in a same group are arranged to be separated by XRD detectors in other groups, and wherein rays of each of the radiation source focus points are merely received by XRD detectors having the same group number as the radiation source focus point.

According to another aspect of the present disclosure, there is provided a detection method, comprising: irradiating, by a distributed radiation source, an object under detection, wherein the distributed radiation source has a plurality of radiation source focus points and the radiation source focus points are divided into a certain number of groups; dividing a plurality of XRD detectors of an XRD detection device into the same number of groups as the radiation source focus points, wherein XRD detectors in a same group are arranged to be separated by XRD detectors in other groups; and controlling, by a primary collimator when a radiation source focus point is emitting rays, such that rays emitted by the radiation source focus point are merely received by XRD detectors having the same group number as the radiation source focus point in the plurality of XRD detectors.

BRIEF DESCRIPTION OF THE DRAWINGS

Features and advantages of the disclosure would be better understood by referring to the accompanying drawings. It is to be understood that the accompanying drawings are exemplary only, and are not restrictive of the present disclosure. In these drawings:

FIG. 13 is a schematic diagram illustrating the state of a detection system performing XRD detection according to some embodiments of the disclosure.

FIG. 14 is a flow chart illustrating a detection method according to some embodiments of the disclosure.

DETAILED DESCRIPTION OF ILLUSTRATIVE IMPLEMENTATIONS

In the following detailed description, numerous specific details are set forth in order to provide a thorough understanding of the present application. However, it is obvious for those skilled in the art that the present application can be practiced without some of the specific details. The embodiments are merely examples and the present application is not limited to the specific configurations and algorithms set forth in the example embodiments. However, the present application can cover various modification, replacement and improvement of elements, components and algorithms, without departing from the scope of the present application.

In the following descriptions, FIGS. 1-4 will be referred to illustrate the detection system and method according to the embodiments of the present disclosure.

Figure 1:
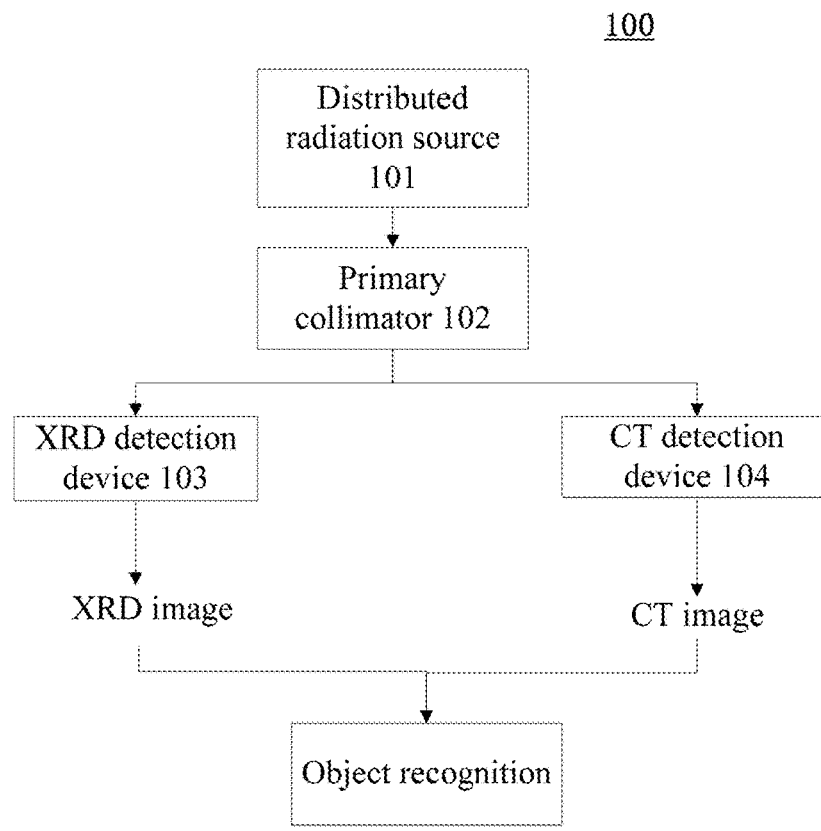
FIG. 1 is a block diagram illustrating a detection system according to some embodiments of the disclosure.

FIG. 1 is a block diagram illustrating a detection system 100 according to some embodiments of the disclosure. As shown in FIG. 1, the detection system 100 of this embodiment may include: a distributed radiation source 101 configured to irradiate an object under detection; a primary collimator 102 configured to separate rays of the distributed radiation source 101 into two parts, wherein one part is for the XRD detection and the other part is for the CT detection; an XRD detection device 103 configured to perform XRD detection to obtain an XRD image; and a CT detection device 104 configured to perform a CT detection to obtain a CT image, wherein the XRD detection and the CT detection are performed simultaneously.

In some embodiments, the primary collimator may be a primary collimator with two openings, so as to separate the rays of the distributed radiation source into two parts, in which one part is for CT detection and the other part is for XRD detection. However, it should be understood that such separation performed by the primary collimator in association with the rays of the distributed radiation source does not necessarily indicate splitting of the rays into two parts physically, but it is also feasible to form, by the primary collimator, a ray beam with a large cone angle, such that one part of the rays is used for CT detection and another part of the rays is used for XRD detection.

In accordance with the detection system 100 of the embodiment of the disclosure, the XRD detection device 103 and the CT detection device 104 may share one set of distributed radiation source 101 and perform XRD detection and CT detection simultaneously. The XRD image from the XRD detection and the CT image from the CT detection are used for object recognition.

Figure 2:
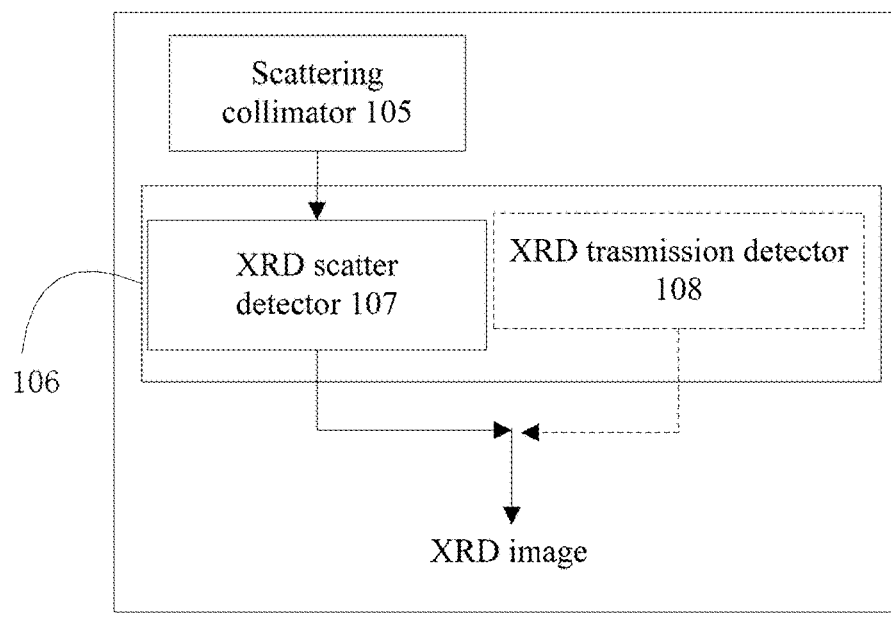
FIG. 2 is a block diagram illustrating a XRD detection device according to some embodiments of the disclosure.

FIG. 2 is a block diagram illustrating the XRD detection device 103 according to some embodiments of the disclosure. As shown in FIG. 2, the XRD detection device 103 may include: at least one XRD detector 106 configured to receive the rays for XRD detection separated by the primary collimator to perform XRD detection so as to obtain an XRD image. The at least one XRD detector 106 may include at least one XRD scattering detector 107 configured to receive scattered rays upon the rays for XRD detection being scattered by an object under detection to perform XRD detection so as to obtain XRD scattering data. In one embodiment, the XRD scattering detector 107 may be a pixilated energy resolving detector, such as a linear array detector.

It should be understood that the XRD scattering detector 107 doesn't receive the scattered rays in all the scattering directions, but only the scattered rays in a certain direction (i.e., with a certain scattering angle). As such, a scattering collimator 105 is provided in front of the XRD scattering detector 107 for selecting the rays having a certain scattering direction from the rays for XRD detection upon being scattered by an object under detection.

In one embodiment, the at least one XRD detector 106 may further include: at least one XRD transmission detector 108 configured to receive transmitted rays from the rays for XRD detection upon transmitting through the object under detection to perform XRD detection so as to obtain XRD transmission data. The XRD transmission data may be used to calibrate the measurement results of the XRD scattering detector 107 to obtain more plentiful and accurate information of the object under detection.

Figure 3:
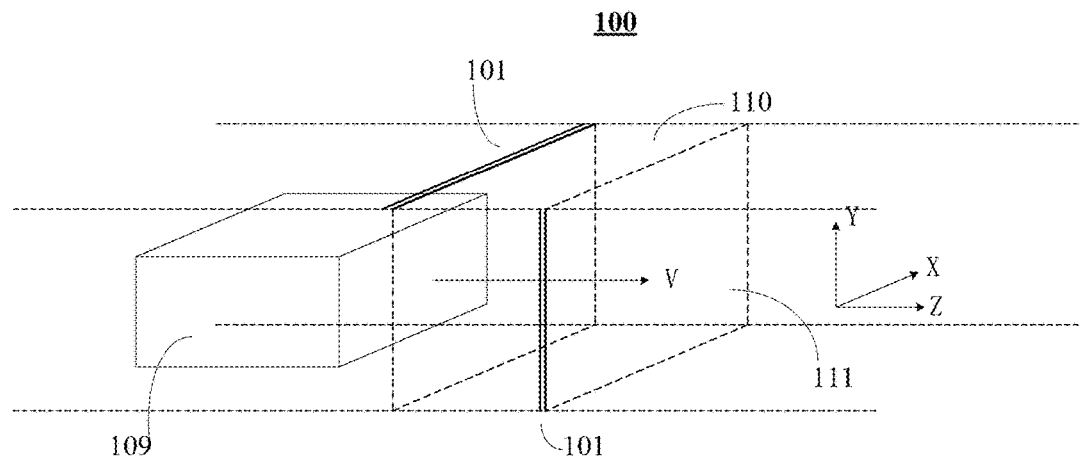
FIG. 3 is a schematic diagram illustrating the application of a detection system according to some embodiments of the disclosure.

FIG. 3 is a schematic diagram illustrating the application of the detection system 100 according to some embodiments of the disclosure. As shown in FIG. 3, the object under detection 109 may pass through the transfer passage 111 by moving along a conveyor belt towards the Z direction with a certain speed V. It's to be understood that an XYZ coordinate system is given in FIG. 3, wherein Z-direction is the direction towards which the conveyor belt moves, Y-direction is the direction perpendicular to the plane of the conveyor belt, and X-direction is the direction perpendicular to the plane established by Y and Z.

As shown in FIG. 3, the detection system 100 may include a distributed radiation source 101 which irradiates an object under detection 109. In FIG. 3, two distributed radiation sources 101 are shown, but it should be understood that the detection system may include more or less distributed radiation sources 101 disposed on at least a part of an internal side of the transfer passage frame structure 110. As shown in FIG. 3, one of the two distributed radiation sources 101 is disposed at the edge of the top wall inside the transfer passage frame structure 110, and the other is disposed at the edge of the side wall inside the transfer passage frame structure 110. However, it should be understood the positions of the distributed radiation sources 101 are not limited to this, for example, the distributed radiation sources 101 may be arranged on any positions of the top wall, bottom wall and side wall inside the transfer massage frame structure 110. Moreover, the distributed radiation source 101 may be L-type, U-type, Circle-type or any other suitable types.

The distributed radiation source 101 may have a plurality of radiation source focus points thereon which may be activated independently to emit rays. It should be understood the how these radiation source focus points are activated, such as the activation order and the combination form, can be controlled by a distributed radiation source control device or control program. In addition, in the case of a plurality of distributed radiation sources 101, these distributed radiation sources 101 may have the same or different number of the radiation source focus points.

It should be noted that, when the detection system 100 includes a plurality of distributed radiation sources 101, the system 100 may include a primary collimator 102, an XRD detection device 103 and a CT detection device 104 corresponding to each of the distributed radiation sources 101. For each of the plurality of distributed radiation sources, the primary collimator 102 is arranged between the distributed radiation source 101 and the object under detection 109, and the XRD detection device 103 and CT detection device 104 are arranged such that the object under detection 109 is positioned between the primary collimator 102 and the XRD detection device 103 and CT detection device 104, that is, the XRD detection device 103 and the CT detection device 104 may be arranged at a side of the object under detection 109 opposite to the primary collimator 102. For example, referring FIG. 3, for the distributed radiation source 101 positioned at the edge of the top wall inside the transfer passage frame structure 110, the primary collimator 102 may be arranged between the distributed radiation source 101 and the object under detection 109, and the XRD detection device 103 and the CT detection device 104 may be arranged below the conveyor belt such that the object under detection 109 is located between the primary collimator 102 and the corresponding XRD detection device 103 and CT detection device 104.

In one embodiment, the radiation source focus points on each of the distributed radiation sources emit multiple pencil beams, and these pencil beams are distributed as a fan (from the view of the detectors, they are "inverse fan beam").

Figure 4:
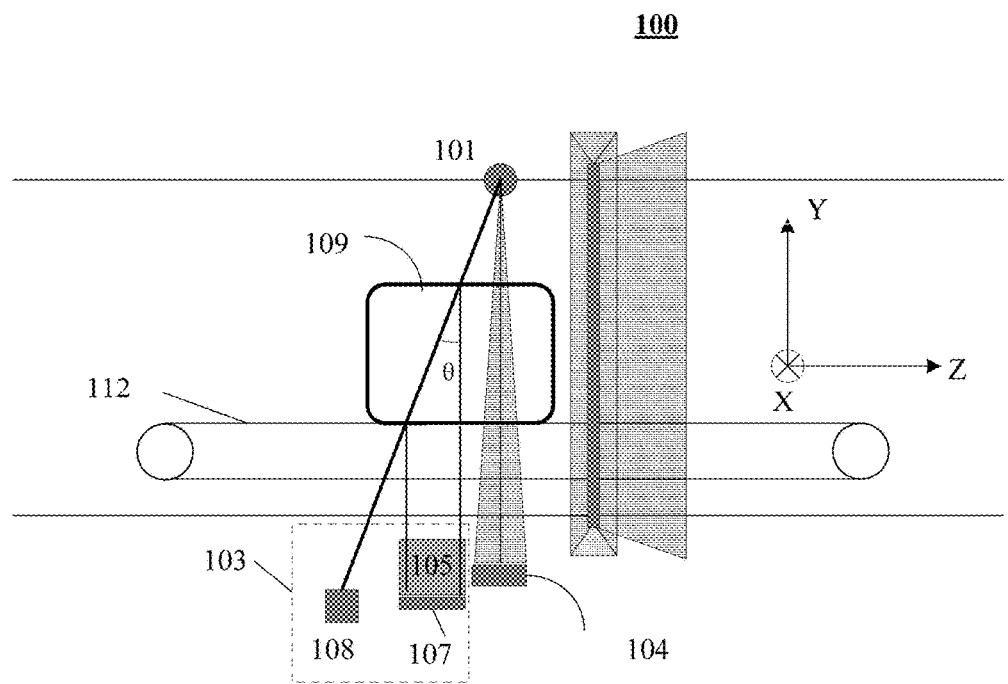
FIG. 4 is a longitudinal section diagram illustrating a detection system according to some embodiments of the disclosure.

FIG. 4 is a longitudinal section diagram illustrating the detection system 100 according to some embodiments of the disclosure. An XYZ coordinate system which is identical to that in FIG. 3 is also shown in FIG. 4, but the X-direction is perpendicular to and toward the paper due to FIG. 4 being a longitudinal section diagram.

As shown in FIG. 4, the object under detection 109 may travel with the conveyor belt 112 towards Z-direction and be irradiated by the distributed radiation source 101. As shown in FIG. 4, the rays emitted by each of radiation source focus points on the distributed radiation sources 101 are separated into two parts: one part emits toward the XRD detection device 103 for XRD detection and the other part emits toward the CT detection device 104 for CT detection. As described above, the separation of the rays is completed substantially by the primary collimator 102 (not shown in FIG. 4) arranged between the distributed radiation source 101 and the object under detection 109. There may exist a certain angle between radiation planes of these two parts of rays separated by the primary collimator 102, such that the XRD detection and the CT detection don't interfere with each other. Accordingly, the XRD detection and the CT detection can be performed simultaneously.

As shown in FIG. 4, for the XRD detection, the XRD detection device 103 may include at least one XRD scattering detector 107 configured to receive scattered rays from the rays for XRD detection upon being scattered by the object under detection 109 to perform XRD detection so as to obtain XRD scattering data. As described above, it should be noted that the XRD scattering detector 107 doesn't receive scattered rays in all scattering directions, but only the scattered rays in a certain direction (i.e., with a certain scattering angle). In FIG. 4, the XRD scattering detector 107 may only receive scattered rays having a scattering angle θ scattered by points on the object under detection 109 (i.e., the angle between the incident rays emitted to points on the object under detection 109 and the scattered rays scattered by each of the points). As such, a scattering collimator 105 may be arranged in front of the XRD scattering detector 107. The scattering collimator 105 selects the scattered rays having a scattering angle θ from the rays for XRD detection upon being scattered by points on the object under detection 109, such that the scattered rays enter into the XRD scattering detector 107.

The XRD detection device 103 may further include at least one XRD transmission detector 108 configured to receive transmitted rays upon the rays for XRD detection transmitting through an object under detection to perform XRD detection so as to obtain XRD transmission data. The XRD transmission data may be used to calibrate the measurement results of the XRD scattering detector 107 to obtain more plentiful and accurate information of the object under detection 109. It should be understood that the direction of the transmitted rays is the direction of the incident rays emitting to the object under detection 109.

In addition, as shown in FIG. 4, the XRD transmission detector 108 may be arranged on the same plane (i.e., the XY-plane in FIG. 4) with the distributed radiation source 101. The XRD scattering detector 107 and corresponding XRD transmission detector 108 may have the same X-coordinate and Y-coordinate but stagger in the Z direction a certain distance (the distance is determined in dependence on the scattering angle θ). That is, the XRD scattering detector 107 can be arranged on a plane parallel to the XY plane but having a certain distance from the XY plane in Z-direction.

Figure 5:
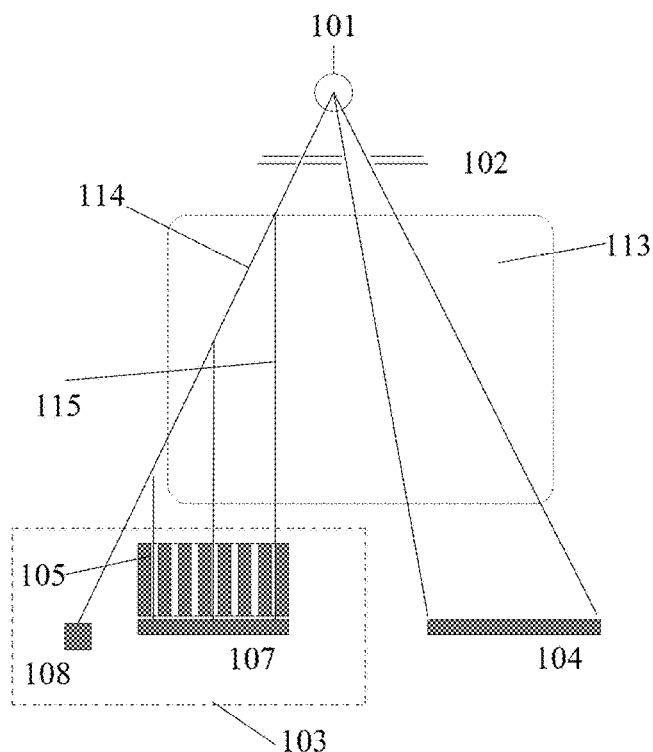
FIG. 5 is a schematic diagram illustrating the imaging principle according to some embodiments of the disclosure.

FIG. 5 is a schematic diagram illustrating the imaging principle according to some embodiments of the disclosure. In FIG. 5, the reference number 113 refers to the detection region. As shown in FIG. 5, the rays emitted by the distributed radiation source 101 may be separated into two parts: one part is emitted to the XRD detection device 103 for XRD detection and the other part is emitted to the CT detection device 104 for CT detection. The radiation planes of the two parts of rays separated by the primary collimator may have a certain angle so that the XRD detection and the CT detection don't interfere with each other. Accordingly, the XRD detection and the CT detection can be performed simultaneously.

Consistent with FIG. 4, for the XRD detection, the XRD detection device 103 may include at least one XRD scattering detector 107 configured to receive scattered rays of the rays for XRD detection upon being scattered by an object under detection 109 to perform XRD detection so as to obtain XRD scattering data. As described above, it should be understood that the XRD scattering detector 107 doesn't receive the scattered rays in all scattering directions, but only the scattered rays in a certain direction (i.e., with a certain scattering angle). In FIG. 5, the XRD scattering detector 107 may only receive scattered rays with a scattering angle θ scattered from the points on the object under detection 109 (i.e., the angle between the incident rays 114 emitting to points on the object under detection 109 and the scattered rays 115 scattered by each of the points). As such, a scattering collimator 105 may be arranged in front of the XRD scattering detector 107. The scattering collimator 105 selects the scattered rays having a scattering angle θ from the rays for XRD detection being scattered from points on the object under detection 109, such that the selected scattered rays enter into the XRD scattering detector 107. Similarly, the XRD detection device 103 may further include at least one XRD transmission detector 108 configured to receive transmitted rays of the rays for XRD detection upon transmitting through the object under detection to perform XRD detection so as to obtain XRD transmission data. The XRD transmission data may be used to calibrate the measurement results of the XRD scattering detector 108 to obtain more plentiful and accurate information of the object under detection 109. It should be understood that the direction of the transmitted rays is the direction of the incident rays 114 emitting to the object under detection 109.

As described above, the detection system 100 of the embodiments of the present disclosure may obtain XRD detection information and CT detection information simultaneously during the distributed radiation source focus points are activated. Accordingly, the system 100 may integrate the CT detection system and the XRD detection system and combine the traditional multiple levels of detections together. Moreover, the CT detection system and the XRD detection system share a set of distributed radiation source, a CT image and an XRD image can be obtained simultaneously. Therefore, the size of the system can be reduced and the detection efficiency can be improved, as compared with a multi-level detection system. In addition, the accuracy of data matching in multi-modality imaging can be improved, and both the false positive rate and the false negative rate of the system can be decreased.

On the other hand, in the detection system 100 of the embodiments of the disclosure, the aggregation way of the scattered rays is somewhat complex, so it is difficult to design and manufactory the scattering collimator such that the scattered rays from all points (the scattering centers) on the object under detection have an equal scattering angle. Although the scattering collimator may utilize a multi-leaf and slit scattering collimator, which is easy to design and manufacture, the crosstalk problem still exists inevitably, that is, the scattered rays from adjacent scattering centers may enter into a same XRD detection device. As described in the Background section, in US2011/0188632A1, the primary collimator separate the rays for XRD detection onto multiple planes and the scattering collimators and the detector are arranged in a staggered manner to reduce the impacts of crosstalk, however, this design increases the number of the scattering collimators, the complexity of the primary collimator and the size of the system. In addition, in the mode of inverse fan beam, the utilization of the multi-leaf and slit scattering collimators may result in deviation of actual scattering angles at different positions, which may reduce the angular resolution.

In one embodiment, the radiation source focus points on the distributed radiation source and the XRD detection devices are divided into a certain number of groups, respectively, and the rays of each of the radiation source focus points only emit into the XRD detection devices having the same group number with the radiation source focus point, so as to reduce crosstalk between rays.

Figure 6:
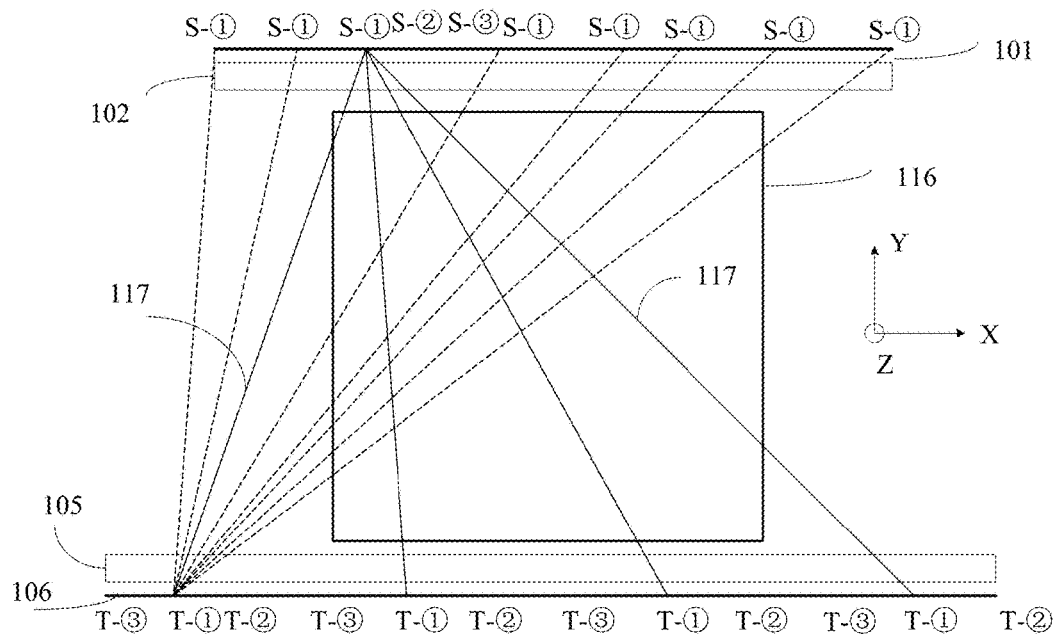
FIG. 6 is a schematic diagram illustrating a grouping arrangement of radiation source focus points and XRD imaging devices according to some embodiments of the disclosure.

FIG. 6 is a schematic diagram illustrating a grouping arrangement of radiation source focus points and XRD detection devices according to some embodiments of the disclosure. It should be noted that FIG. 6 only shows the XRD detection plane, wherein the reference number 116 refers to an XRD detection region. An XYZ coordinate system which is identical with that in FIG. 3 is also shown in FIG. 6, but it should be noted that the XRD detection plane is in the X-Y plane.

As shown in FIG. 6, there are a plurality of radiation source focus points on the distributed radiation source 101, and the plurality of radiation source focus points are divided into a certain number of groups. In this example, the radiation source focus points on the distributed radiation source 101 are divided into 3 groups, for example, which are shown as S-①, S-② and S-③. Moreover, with constraint of the primary collimator 102, each of the radiation source focus points emits a number of pencil beams 117 in the XRD detection plane, and these pencil beams 117 are distributed as a fan. FIG. 6 shows 4 pencil beams, but it should be understood that there might be several pencil beams in practice.

In addition, as shown in FIG. 6, the pencil beams, distributed as a fan, may emit to the XRD detector 106 via the scattering collimator 105. However, it should be noted, in practice, the scattering collimator is only arranged above the XRD scattering detector to enable only the scattered rays with a certain scattering angle from the scattered rays emitted by each of the scattering centers to enter into the XRD scattering detector, as described above. The XRD detectors 106 are also divided into different groups, the number of which is the same as the group number of the radiation source focus points on the distributed radiation source 101. For example, in the case that the radiation source focus points are divided into 3 groups, the XRD detectors are also divided into 3 groups, for example, shown as T-①, T-② and T-③.

The XRD detectors 106 in a same group can be arranged in the manner of being separated by the XRD detectors in other groups. Specifically, as shown in FIG. 6, the XRD detectors in group T-① are arranged in the manner of being separated by the XRD detectors in group T-② and group T-③. That is, these XRD detectors 106 are arranged in the order of one XRD detector in group T-①, one XRD detector in group T-② and one XRD detector in group T-③ in a circular manner.

Figure 7:
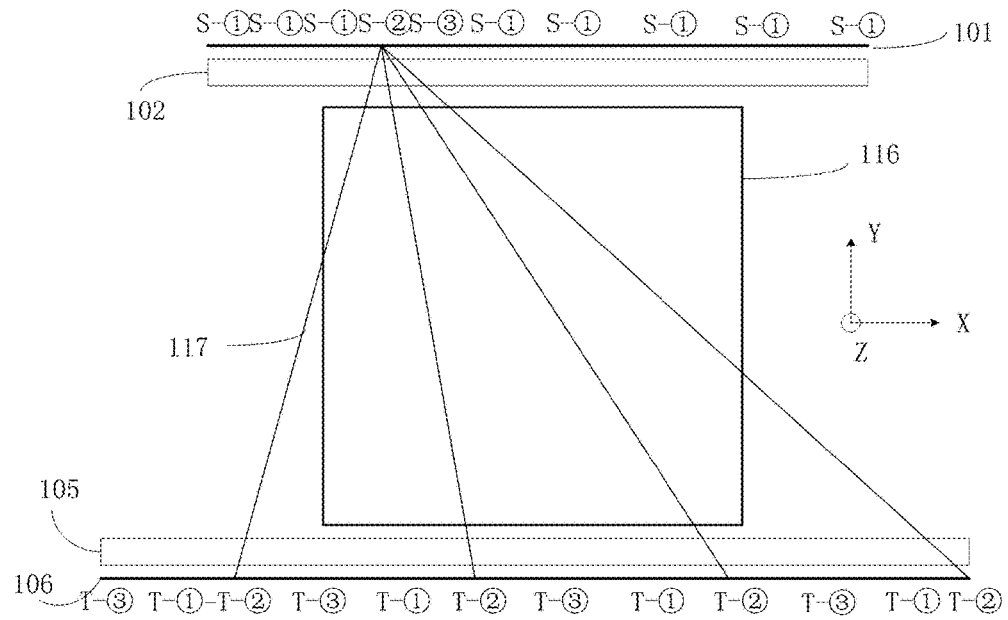
FIG. 7 is a schematic diagram illustrating a grouping arrangement of radiation source focus points and XRD imaging devices according to some embodiments of the disclosure.
Figure 8:
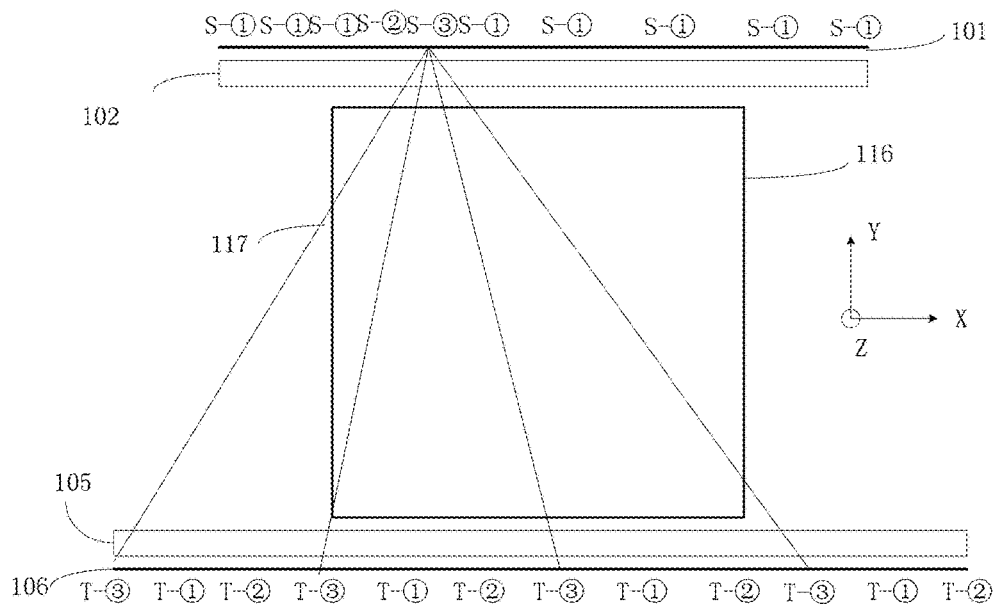
FIG. 8 is a schematic diagram illustrating a grouping arrangement of radiation source focus points and XRD imaging devices according to some embodiments of the disclosure.

The rays emitted by each of the radiation source focus points on the distributed radiation source 101 emit into the XRD detectors which has the same group number with the radiation source focus point. For example, as shown in FIG. 6, the pencil beams emitted by the radiation source focus point in group S-① only enter into the XRD detectors in group T-①. Furthermore, as shown in FIG. 7 and FIG. 8, the pencil beams emitted by the radiation source focus point in group S-② only enter into the XRD detectors in group T-②, and the pencil beams emitted by the radiation source focus point in group S-③ only enter into the XRD detectors in group T-③.

In the detection device of the embodiments of the disclosure, the distributed radiation source 101 enable the radiation source focus points to be activated in a certain order to emit X rays according to requirements of CT detection. Within the XRD detection plane, the radiation source focus point emits a number of pencil beams under constraint of the primary collimator 102, as shown with solid lines in the figure. These pencil beams are distributed as a fan, cover most of the XRD detection region and are aligned to the XRD detectors having the same group number in different positions. In practice, when a radiation source focus point is emitting rays, the XRD detectors having the same group number as the radiation source focus point start to count and the XRD detectors having other group numbers keep silent, so that the rays from this radiation source focus point emit to the XRD detectors having the same group number only. Each of the XRD detectors can receive the rays from at least one activated radiation source focus point having the same group number, so these rays may form "inverse fan beam" from the perspective of each of the XRD detectors, as shown with the dotted lines in the FIG. 6.

As previously mentioned, the XRD detector 106 may include XRD scattering detectors 107 and XRD transmission detector 108. The XRD transmission detectors 108 may be arranged on the same plane (i.e., the X-Y plane in FIG. 4) as the distributed radiation source 101. The XRD scattering detectors 107 may have the same X-coordinate and Y-coordinate as the corresponding XRD transmission detectors 108, but stagger a certain distance in the Z direction, (the distance is in dependence on the scattering angle θ). When a radiation source focus point is emitting rays, the transmission detectors in the XRD detectors having the same group number measure the XRD transmission data for the incident rays 117, and the respective detector units of the scattering detectors in corresponding positions measure the XRD scattering data for the incident rays upon scattered by scattering centers at different depths along Y axis.

Figure 9:
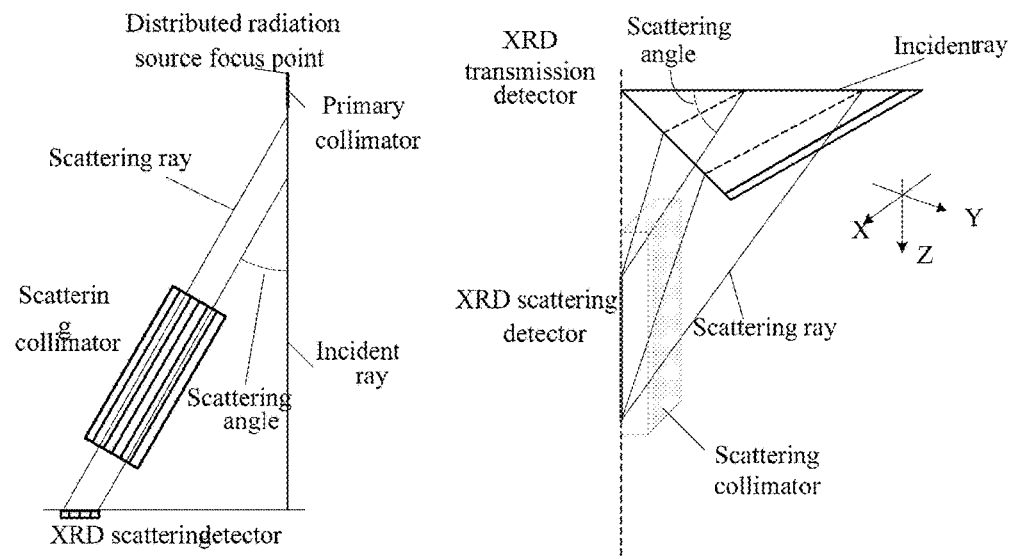
FIG. 9 is a schematic diagram illustrating the principle of an XRD scattering detector detecting rays through a scattering collimator according to some embodiments of the disclosure.

FIG. 9 is a schematic diagram illustrating the principle of an XRD scattering detector detecting rays through a scattering collimator according to some embodiments of the disclosure from a different view. As shown in FIG. 9, with respect to one XRD detector which may include an XRD transmission detector and a corresponding XRD scattering detector, rays emitted at different time are in the form of "inverse fan beam", as shown in the right side of FIG. 9, and the scattered rays from a single incident ray at different Y-axis depths but having the same scattering angle enter into respective detector units of the XRD scattering detector along the slits between multiple leaves of the scattering collimator, as shown in the left side of FIG. 9. Here, the slits between multiple leaves of the scattering collimator allow the entered scattered rays to form a set of parallel planes intersecting with the incident ray, as shown in the right side of FIG. 9.

According to the detection device of the embodiments of the disclosure, the radiation source focus points on the distributed radiation source 101 and the XRD detectors 106 are divided into groups with respective group numbers and operate with binding of the group numbers, and meanwhile the different groups of XRD detectors 106 are alternatively arranged, so the rays from a radiation source focus point emit to the XRD detectors having the same group number with the radiation source focus point, and thereby crosstalk between scattered rays can be avoided.

Figure 10:
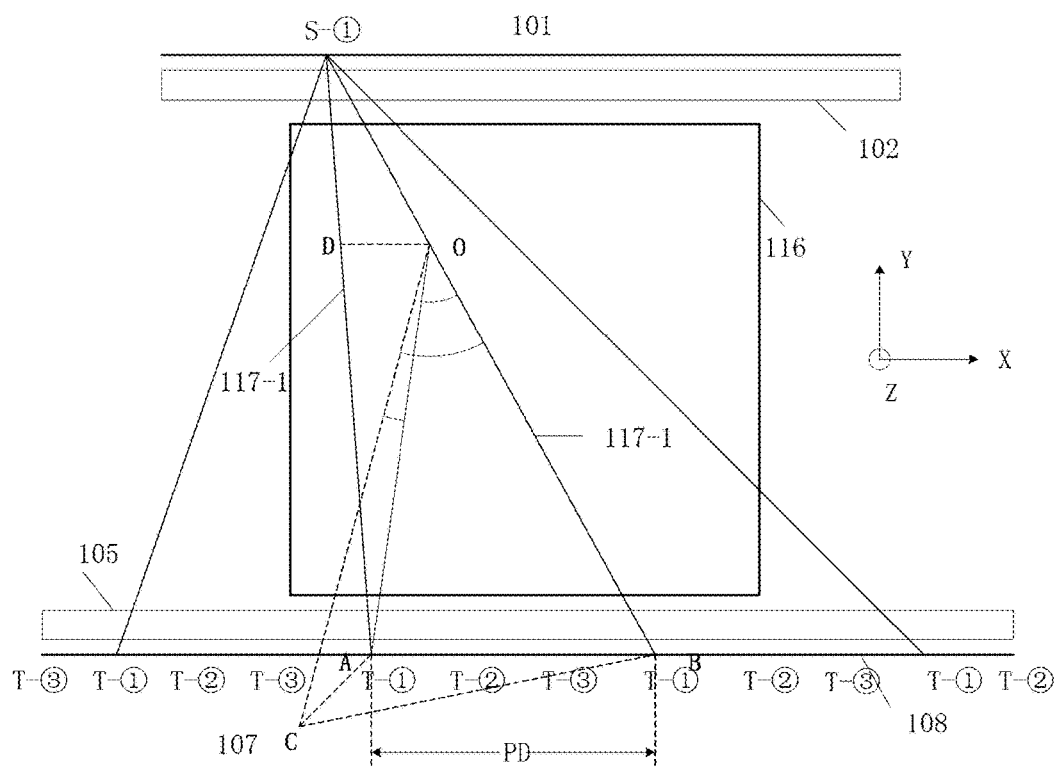
FIG. 10 is a schematic diagram illustrating the principle of avoiding crosstalk by a detection device according to some embodiments of the disclosure.

FIG. 10 is a schematic diagram illustrating the principle of avoiding crosstalk by a detection device according to some embodiments of the disclosure. As shown in FIG. 10, the rays from the radiation source focus point with the group number S-① on the distributed radiation source 101, with constraint of the primary collimator 102, enter into the XRD detectors with the group number T-①. As shown in the figure, the number of rays include an incident ray 117-1 and an incident ray 117-2, and are distributed as a fan.

As mentioned, each XRD detector 106 may include an XRD transmission detector 108 which may be on the XY plane, and an XRD scattering detector 107 which may have the same X-coordinate and Y-coordinate as the corresponding XRD transmission detector 108 but stagger a certain distance in the Z direction. In FIG. 10, a XRD transmission detector 108 is located at point A, and the corresponding scattering detector 107 is located at point C and receives the scattered rays of the incident ray 117-1 from point D; and another XRD transmission detector 108 is located at point B and the corresponding XRD scattered detector 107 receives the scattered rays of the incident ray 117-2 from point O. However, the scattered rays of the incident ray 117-2 from point O may enter into the XRD scattering detector located at point C due to the multi-leaf and slit design of the scattering collimator 105, which results in crosstalk.

Specifically, it may be derived from the geometrical relationship shown in FIG. 10 that the scattering angle of the scattered line OC is ∠BOC:

$$\angle BOC = \cos^{-1}(\cos \angle AOC \cdot \cos \angle AOB) \quad (1.1)$$

where ∠BOC>∠AOB XRD detection measures coherent scattering of photos by an object, in which a key relationship is:

$$q = E \sin(\theta/2)/(hc) \quad (1.2)$$

where q is a scattering factor, E represents the energy of the scattered photos, θ represents the scattering angle, h and c represent the Planck constant and the light speed respectively. Different objects have distinctness in XRD spectrum that is distributed based on the factor q. The interference (diffraction) effect of the coherence scattering of the object may be reduced gradually after q is increased to some degree. If the scattering angle is large, the spectra section having significant diffraction information about the object will be compressed to a smaller energy interval. And when the scattering angle increases to some degree, the valid XRD spectrum can be ignored due to being outside an interested energy interval. Therefore, the common method for reducing crosstalk is to increase the scattering angle ∠BOC, and the easiest way is to increase the distance $P_D$ between detectors along X-direction.

The increase of $P_D$ may decrease crosstalk, but for a system in which the radiation source focus points and the detectors are not grouped and the detectors at A and B are not arranged in a staggered manner, it causes some problems. For example, if the number of detectors are decreased significantly due to excessive increase of $P_D$, rays emitted by a radiation source focus point in the XRD detection plane will decrease dramatically, which causes the rays for XRD detection have reduced ray intensity, decreased and non-uniform coverage area. In addition, staggering of the adjacent detectors in the Z direction by decreasing $P_D$ (as illustrated in US2011/0188632A1, a primary collimator separate the rays for XRD detection into multiple planes, and scattering collimators and detectors are arranged in a staggered manner) may avoid crosstalk to some degree, but it requires additional scattering collimators and complex design of the primary collimator, and causes the size of the system larger.

The detection system according to embodiments of the disclosure divide the radiation source focus points on the distribute radiation source and detectors into same number of groups, wherein the detectors in a group are arranged to be separated by the detectors in other groups, and the radiation source focus points and the detectors are bound via group numbers to operate, that is, the rays emitted by a ray focus point are emitted into those detectors having the same group number only, as shown in FIG. 6~8, the detectors with the group number T-① are separated by the detectors having the group number T-② or T-③ therebetween, and the distance between adjacent detectors remain the same so that the distance between the detectors having the same group number may be increased by times, and thereby the scattering angle of the rays causing crosstalk is big enough. With such design, $P_D$ can be increased with assurance of sufficient number of detectors and ray intensity and uniformity in the detection plane. Moreover, the design of the scattering collimator can be kept unchanged without additional scattering collimators, so the size and complexity of the system would not be increased.

It should be understood, in the above description, the radiation source focus points of the radiation source and the XRD detectors are divided into 3 groups, however, they can be divided into more or less groups. In addition, in the above description, the XRD detectors in a same group are arranged to be separated by the XRD detectors in other groups, but it should be understood that the XRD detectors in a same group may also be arranged to be separated by part of the XRD detectors in other groups, such as, in a manner of one XRD detector in group T-①, one XRD detector in group T-②, one XRD detector in group T-①, one XRD detector in group T-②, one XRD detector in group T-③, one XRD detector in group T-①. . . It should be noted it's merely exemplary and the arrangement manner of the XRD detectors is not limited thereto. Of course, the more the number of groups is, the larger the distance between two detectors within a same group is, and thereby crosstalk can be avoided to a greater extent.

Figure 11:
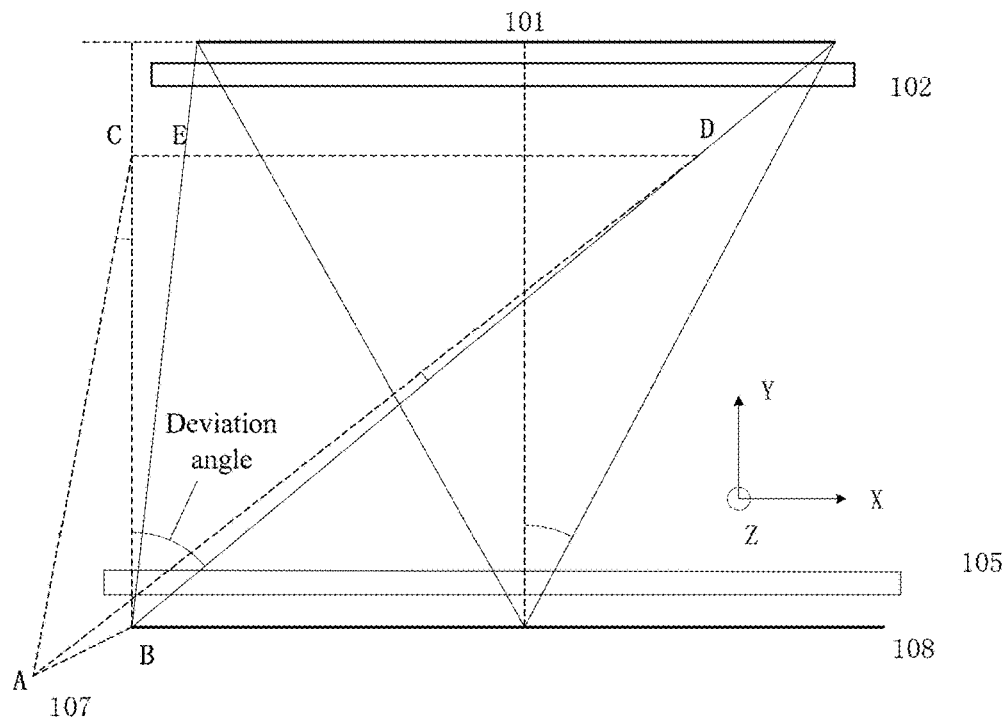
FIG. 11 is a schematic diagram illustrating the principle of causing angle deviation by a multi-leaf and slit scattering collimator according to some embodiments of the disclosure.

FIG. 11 is a schematic diagram illustrating the principle of causing angle deviation by a multi-leaf and slit scattering collimator according to some embodiments of the disclosure. As shown in FIG. 11, the scattering detector 107 located at position A may measure scattering rays from crossover points (e.g., E, D, i.e., scattering centers) of the straight line CD with each of the incident rays (e.g., EB, DB). Assuming that the predetermined scattering angle of the system is ∠ACB=θ, but in fact, the scattering angle θADB of the scattering ray AD is:

$$\angle ADB = \tan^{-1}(\cos(\angle CBD)\tan\theta) \quad (1.3)$$

therefore ∠ACB<θ. If the predetermined scattering angle of the system is θ=3° and the deviation angle is ∠CBD=30°, ∠ADB≈2.60°; if ∠CBD=20°, ∠ADB≈2.82°. Thus, the deviation angle ∠CBD generated due to the incident ray DB being not perpendicular to the ray CD results in deviation of the actual scattering angles. The deviation angles in different positions are different, so the actual scattering angles in different positions are not equal, especially the positions located at the two sides of the detection region near the edges. The decrease of the deviation angle ∠CBD may decrease the deviation of the actual scattering angle from the designed scattering angle effectively to improve the angular resolution.

Figure 12:
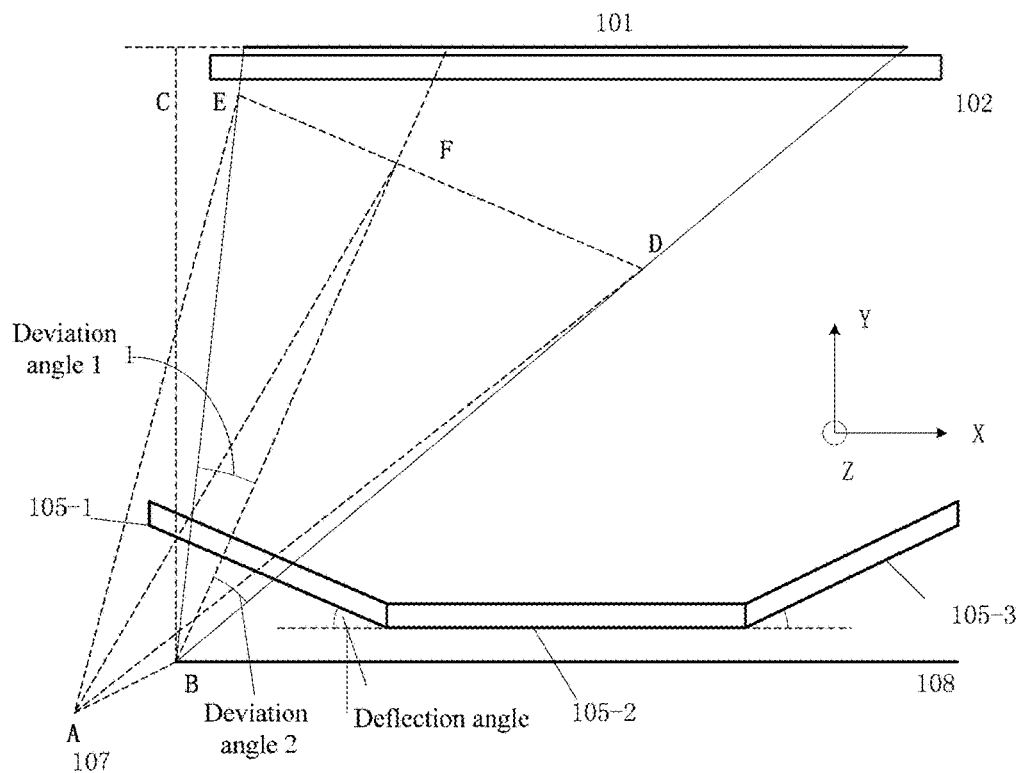
FIG. 12 is a schematic diagram illustrating the principle of avoiding the angular deviation by a detection system according to some embodiments of the disclosure.

FIG. 12 is a schematic diagram illustrating principle(s) of avoiding the angular deviation by a detection system according to some embodiments of the disclosure. As shown in FIG. 12, the scattering collimator 105 has a form of three segments, i.e., it is divided into three segments 105-1, 105-2 and 105-3, and employs a design being shaped as a polygonal line with multiple leaves and slits. The segments 105-1 and 105-3 at the two sides have a certain deflection angle with an extended line of the middle section 105-2 respectively. The deflection angle may be in a range of 5° to 40°, and preferably, in a range of 10° to 20°. The leaves of the segment 105-1 may enable the incoming scattered rays to form several parallel planes, one of which intersects with the detection plane at line ED. If the line BF is perpendicular to the line ED, ∠AFB=θ. As discussed above, the maximal deviation angles (∠EBF and ∠DBF) are decreased significantly compared with the foregoing deviation angle ∠CBD (reduce at least half). According to the equation (1.3), the maximal deviation angle of the actual scattering angle from the predetermined scattering angel of the system is decreased significantly so that the angular resolution of the system can be improved without adjustment of any design for other structures of the system.

FIG. 13 is a schematic diagram illustrating the state of a detection system performing XRD detection according to some embodiments of the disclosure, which shows the design and position of the primary collimator, position of the detection region and the arrangement of the scattering collimators and XRD detectors. As shown in FIG. 13, all the radiation source focus points on the distributed radiation source 101 and all the XRD detectors are grouped and numbered. The radiation source focus points emit X-rays in a certain order as required by CT imaging, and when the radiation source focus points with a certain group number are emitting rays, the detectors having the same number detect data while other detectors keep silent. The rays emitted by each of the focus points may form several pencil beams directing at transmission detectors in the detectors having the same group number under constraint of the primary collimator 102. When the rays emitted by each of the focus points are drawn on the plane of the XRD detection region all at once, the distribution of the rays is shown as FIG. 13. The incident rays have several aggregation points at positions close to the radiation source, so a primary collimator 102 is arranged at a corresponding height along Y-axis. Due to the height at which the aggregation points appear is affected by the number of groups of the detectors and the radiation source focus points and the geometrical relationship of the system, etc., the primary collimator 102 may include at least one collimator, and the at least one collimator may be arranged at the aggregation points of the rays emitted by each of the radiation source focus points, so that when each of the radiation source focus points is emitting rays, the rays emitted by each of the radiation source focus points, under control of the primary collimator, are merely received by the XRD detectors in the plurality of XRD detectors that have the same group number as that of the radiation source focus point. For example, as shown in FIG. 13, the shown primary collimator 102 includes two collimators 102-1 and 102-2. Specifically, the first collimator 102-1 is arranged at the aggregation points of the rays emitted by the radiation source focus points, and the second collimator 102-2 is arranged at the aggregation points of the rays from the first collimator.

The primary collimator 102 may be made of materials that can strongly absorb X-rays and has apertures at aggregation points of rays. The scattering collimator 105 has a design being shaped as a polygonal line and having multiple leaves and slits. The number of the slits equal to or more than the number of pixels subdivided in the detection region along Y-axis. The transmission detectors and the scattering detectors are arranged below the scattering collimator. The scattering detectors have the same X-coordinate and Y-coordinate as their respective corresponding transmission detectors, but stagger a certain distance in the Z-direction from their respective corresponding transmission detectors.

Typically, the number of the radiation source focus points is significant larger than the number of the XRD detector modules, and the distance $W_{sc}$ between adjacent focus points is less than the distance $W_D$ between adjacent detectors due to a set of distributed radiation source shared by the XRD detection and the CT detection which requires more radiation source focus points, therefore the upper half section within the detection region has relatively intensive rays. As shown in FIG. 13, intensity of rays in the whole detection plane is relatively uniform, and then $W_{sc}$ and $W_D$ can be adjusted to enable distribution density of rays in the lower half section meet requirements. In the case where the detectors in different groups are arranged alternatively in the order of group number, the minimal distance between the detectors having the same group number is $P_D=NW_D$, wherein N is the number of the groups. Therefore, $P_D$ may be improved effectively by appropriately increasing the number of the groups to reduce the impacts of crosstalk.

As described above, the detection system in accordance with the embodiments of the present disclosure, can perform material recognition based on information about materials obtained from both the two detections (i.e., CT detection and XRD detection), wherein the CT detection and the XRD detection are performed simultaneously rather than an approach of "CT first, XRD second" and share a set of distributed radiation source, thus size of the system can be reduced and detection efficiency, stability and accuracy can be improved, and moreover, both the false positive rate and the false negative rate of the system can be decreased. In addition, the detection device in accordance with the embodiments of the disclosure can avoid the problem of crosstalk between scattered rays of adjacent XRD detectors due to the numbering and binding of the radiation source focus points on the distributed radiation source and the XRD detectors in groups and the alternative arrangement of the XRD detectors. Moreover, the deviation of the actual scattering angle from the designed scattering angle for the system can be decreased due to the polygonal line shaped scattering collimator.

The system has been described above in accordance with embodiments of the disclosure, and a detection method will be described below in accordance with embodiments of the disclosure. FIG. 14 shows a detection method 200 according to some embodiments of the disclosure. As shown in FIG. 14, at step S201, an object under detection is irradiated by a distributed radiation source, wherein the distributed radiation source have a plurality of radiation source focus points and the plurality of radiation source focus points are divided into a certain number of groups. At step S202, a plurality of XRD detectors of an XRD detection device are divided into groups, the number of which is the same as the number of the groups of the radiation source focus points, and the XRD detectors in a same group are arranged in the manner of being separated by the XRD detectors in other groups. At step S203, when each of the radiation source focus points is emitting rays, the rays emitted by each of the radiation source focus points are controlled by the primary collimator to be merely received by the XRD detectors having the same group number in the plurality of XRD detectors as the group number of the radiation source focus point.

In one embodiment, the detection method 200 may further include: separating rays of each of the radiation source focus points into two parts by using the primary collimator, one part is for XRD detection and the other part is for CT detection, and wherein the CT detection and the XRD detection are performed simultaneously.

In some embodiments, the radiation source focus points are independently activated to emit rays.

In some embodiments, the rays of each of the radiation source focus points form pencil beams distributed as a fan, and each of the pencil beams emits into the XRD detectors having the same group number as the radiation source focus point.

In some embodiments, the XRD detection device may include an XRD scattering detector, and the XRD detection may include: detecting, by the XRD scattering detector, scattered rays scattered by points of the object under detection.

In some embodiments, The XRD detector may include an XRD transmission detector, and the XRD detection may include: detecting, by the XRD transmission detector, transmitted rays transmitting through the object under detection.

In some embodiments, the detection method 200 may further include: selecting, by a scattering collimator, scattered rays having a certain scattering angle from the rays for XRD detection upon being scattered by points of the object under detection such that the selected scattered rays emit into the XRD scattering detectors.

In some embodiments, the scattering collimator may have a form of three segments, wherein each of segments at two sides has a certain angle with a middle segment. The angle may be in a range of 10° to 20°.

In some embodiments, the radiation source focus points on the distributed radiation source and the XRD detectors are divided into three groups respectively, and the plurality of XRD detectors are arranged recurrently in the order of an XRD detector in a first group, an XRD detector in a second group, and an XRD detector in a third group.

In some embodiments, the primary collimator may include two collimators, wherein the first collimator is arranged at the aggregation points of the rays emitted by the radiation source focus points, and the second collimator is arranged at the aggregation points of the rays through the first collimator.

It should be understood that the detection system and method of the embodiments of the present disclosure may be applied in the field of security detection. However, those skilled in the art would understood that the detection system and method in accordance with the embodiments of the present disclosure are not limited to the field of security detection, but may also be applied in other relevant fields.

Besides, it should be understood that the XRD detection are described in the case of a multi-modality detection system (i.e., which combines CT detection and XRD detection), however, the XRD detection of the disclosure can be used independently.

It is to be noted that terms "comprising" or "comprises" in the claims do not exclude an element or component that is not listed in the claims. An article "a" or "an" positioned before an element or component also does not exclude existence of multiple of such element or component.

Further, it is to be noted that the language used in the specification has been principally selected for readability and instructional purposes, and it may not have been selected to delineate or circumscribe all of the inventive subject matter. Therefore, a plurality of amendments and variations will be apparent to those skilled in the art without departing from the scope and spirit of the present inventions and appended claims. Accordingly, the disclosure of the above embodiments of the invention is intended to be illustrative, but not limiting, of the scope of the invention. It is intended that the scope of the invention only be limited by the appended claims.

What is claimed is:

1. A detection system, comprising:
    a distributed radiation source having a plurality of radiation source focus points which emit rays to irradiate an object under detection, wherein the plurality of radiation source focus points are divided into a certain number of groups, and wherein the plurality of radiation source focus points are activated independently in an order under control;
    a primary collimator configured to limit rays of each of the radiation source focus points such that the rays emit into an XRD detection device; and
    the XRD detection device including a plurality of XRD detectors, wherein the plurality of XRD detectors are divided into the same number of groups as the radiation source focus points, and XRD detectors in a same group are arranged to be separated by XRD detectors in other groups, and wherein when a radiation source focus point is activated, XRD detectors having the same group number as the radiation source focus point start to count and XRD detectors having other group numbers maintain silence such that rays emitted by the radiation source focus points are merely received by the XRD detectors having the same group number as the radiation source focus point.

2. The detection system of claim 1, wherein the primary collimator separates rays of each of the radiation source focus points into two parts, one part is for XRD detection and the other part is for CT detection, and wherein the CT detection and the XRD detection are performed simultaneously.

3. The detection system of claim 1, wherein the radiation source focus points are independently activated to emit rays.

4. The detection system of claim 3, wherein rays of each of the radiation source focus points form pencil beams distributed as a fan, and each of the pencil beams emits into an XRD detector having the same group number as the radiation source focus point.

5. The detection system of claim 1, the XRD detection device comprises XRD transmission detectors and XRD scattering detectors, wherein the XRD transmission detectors are arranged in a radiation plane of the distributed radiation source, and the XRD scattering detectors are arranged in a plane which parallels to but has a certain distance in a transfer direction of the object under detection from the radiation plane of the distributed radiation source.

6. The detection system of claim 5, wherein the detection system further comprise a scattering collimator, wherein the scattering collimator is configured to select scattered rays having a certain scattering angle from the rays for XRD detection upon being scattered by points of the object under detection such that the selected scattered rays emit into the XRD scattering detectors.

7. The detection system of claim 6, wherein the scattering collimator has a form of three-segments with multiple leaves and slits, and each of segments at two sides has a deflection angle from an extended line of a middle segment.

8. The detection system of claim 7, wherein the deflection angle is in a range of 5° to 40°.

9. The detection system of claim 1, wherein the radiation source focus points on the distributed radiation source and the XRD detectors are divided into three groups respectively, and the plurality of XRD detectors are arranged recurrently in an order of one XRD detector in a first group, one XRD detector in a second group, and one XRD detector in a the third group.

10. The detection system of claim 1, wherein the primary collimator comprises at least one collimator, wherein the at least one collimator is arranged at aggregation points of rays emitted by the radiation source focus points, such that the rays emitted by each of the radiation source focus points are merely received by XRD detectors having the same group number as the radiation source focus point.

11. A detection method, comprising:
irradiating, by a distributed radiation source, an object under detection, wherein the distributed radiation source has a plurality of radiation source focus points and the radiation source focus points are divided into a certain number of groups, and wherein the plurality of radiation source focus points are activated independently in a certain order under control;
dividing a plurality of XRD detectors of an XRD detection device into the same number of groups as the radiation source focus points, wherein XRD detectors in a same group are arranged to be separated by XRD detectors in other groups;
controlling, by a primary collimator when a radiation source focus point is emitting rays, XRD detectors having the same group number as the radiation source focus point start to count and XRD detections having other group numbers maintain silence such that the rays emitted by the radiation source focus points are merely received by the XRD detectors having the same group number as the radiation source focus point.

12. The detection method of claim 11, further comprising: separating rays of each of the radiation source focus points into two parts by the primary collimator, one part is for XRD detection and the other part is for CT detection, and wherein the CT detection and the XRD detection are performed simultaneously.

13. The detection method of claim 11, wherein rays of each of the radiation source focus points form pencil beams distributed as a fan, and each of the pencil beams emits into an XRD detector having the same group number as the radiation source focus point.

14. The detection method of claim 11, wherein the XRD detection device comprises XRD scattering detectors, and the XRD detection comprises: detecting, by the XRD scattering detectors, scattered rays scattered by points of the object under detection.

15. The detection method of claim 14, wherein the XRD detection device further comprises XRD transmission detectors, and the XRD detection comprises: detecting, by the XRD transmission detectors, transmitted rays transmitting through the object under detection.

16. The detection method of claim 14, further comprising: selecting, by a scattering collimator, scattered rays having a certain scattering angle from the rays for XRD detection upon being scattered by points of the object under detection such that the selected scattered rays emit into the XRD scattering detectors.

17. The detection method of claim 14, wherein the scattering collimator has a form of three-segments with multiple leaves and slits, and each of segments at two sides has a deflection angle from an extended line of a middle segment.

18. The detection method of claim 17, wherein the deflection angle is in a range of 5° to 40°.

19. The detection method of claim 11, wherein the radiation source focus points on the distributed radiation source and the XRD detectors are divided into three groups respectively, and the plurality of XRD detectors are arranged recurrently in an order of one XRD detector in a first group, one XRD detector in a second group, and one XRD detector in a third group.

20. The detection method of claim 11, wherein the primary collimator comprises at least one collimator, wherein the at least one collimator is arranged at aggregation points of rays emitted by the radiation source focus points, such that the rays emitted by each of the radiation source focus points are merely received by XRD detectors having the same group number as the radiation source focus point.

* * * * *